United States Patent [19]
Gengler et al.

[11] Patent Number: 5,919,206
[45] Date of Patent: Jul. 6, 1999

[54] SURGICAL TOOL

[75] Inventors: Mark Gengler, Shelby; William W. Sitton, Charlotte, both of N.C.

[73] Assignee: C. M. Wright, Inc., Shelby, N.C.

[21] Appl. No.: 09/027,368

[22] Filed: Feb. 20, 1998

[51] Int. Cl.$^6$ .................................................. A61B 17/28
[52] U.S. Cl. .................. 606/205; 606/206; 606/207; 606/170; 606/171
[58] Field of Search ..................... 606/205, 206, 606/207, 208, 209, 210, 211, 170, 171, 172, 173, 174

[56] References Cited

U.S. PATENT DOCUMENTS

| | | |
|---|---|---|
| 4,522,206 | 6/1985 | Whipple et al. . |
| 5,489,292 | 2/1996 | Tovey et al. ............................ 606/205 |
| 5,496,347 | 3/1996 | Hashiguchi et al. . |
| 5,556,407 | 9/1996 | Wurster et al. . |
| 5,603,724 | 2/1997 | O'Connor . |
| 5,618,294 | 4/1997 | Aust et al. . |
| 5,700,279 | 12/1997 | Benecke ................................. 606/208 |

*Primary Examiner*—Michael Buiz
*Assistant Examiner*—Lien Ngo
*Attorney, Agent, or Firm*—Kennedy, Covington, Lobdell & Hickman, LLP

[57] ABSTRACT

A tool for cutting and/or grasping pieces of food particles or human tissue which includes a pair of jaw members having a first pivot connection and a second camming connection arranged to cause the jaw members to move laterally relative to one another during closing movement thereof, and to cause the closing force applied to the jaw members to increase as the jaw members move relative to one in a closing direction.

5 Claims, 5 Drawing Sheets

5,919,206

SURGICAL TOOL

BACKGROUND OF THE INVENTION

The present invention relates generally to an improved surgical tool for cutting and/or grasping food particles and/or human tissue, and more particularly to a tool of this type that utilizes a pair of cooperating jaw members that have a unique relative motion that offers significant advantages over known tools of this type.

As is well known, food particles (e.g. a piece of meat) sometimes become lodged in the esophagus while a person is eating, and this can become quite serious if the food particle is not removed promptly. One conventional tool presently used for this purpose includes a pair of cup shaped members mounted together with a scissors-like connection which allows the two cup shaped members to move apart and together with a pivotal movement, and the edges of the cup shaped members act as cutting edges when the two members come together. This tool is used by inserting it through an endoscope placed in the throat of the patient, and, using an operating cable extending to the tool, opening and closing the cup shaped members so that, with each such movement, a small piece of the food particle is cut away and retained with the lower cup shaped member, and the lodged particle of food is gradually reduced in size sufficiently that it can be easily dislodged.

This known device has several drawbacks. First, the conventional scissors-type pivot mounting between the cup shaped members inherently results in an ever decreasing closing force between the cup shaped members as they approach one another, with the smallest force being present at the point where the greatest force is required, namely at the point where the cup shaped members are almost in contact with one another and a portion of the food particle is being cut away. Additionally, the circular cutting edges of the cup shaped members is relatively inefficient in terms of a proper cutting action, and, as a result it is often necessary to make a large number of cutting strokes to remove a significant portion of the food particle. Finally, since the cup shaped members must be inserted through an endoscope placed in the esophagus of the patient, they must be small, and, as a result, the volume of the cup-shaped members is quite small and can only hold a limited amount of particles cut from the lodged food particle. Moreover, when the cup-shaped members are full, they must be removed and cleaned, often in the middle of a procedure.

In general, tools of the aforesaid type may also be used as a biopsy tool to remove a portion of a tumor or other human tissue for evaluation after it has been removed, and the above-described drawbacks of such tools are even more pronounced in biopsy applications. For example, if the tool is to be inserted into the body to remove a part of an internal tumor, it must be inserted through a hollow sheath that is small enough to be readily inserted into the body, and therefore the cup shaped member must be very small in size, which exacerbates the problem of having insufficient force to properly cut away a portion of a tumor at the point where the cup shaped members come together at the tumor.

Additionally, other tools of this general type have been proposed which include a pair of laterally extending jaw members that have a pivoted connection at one end of each of the jaw members, and that have some type of lost motion or similar connection that results in a cutting action between the jaw members. Some typical tools of this type are disclosed in U.S. Pat. Nos. 4,887,612; 5,496,347; 5,489,292; 5,556,407; 5,603,724; and 5,618,294. Wile these tools overcome some of the drawbacks of the above-described cup shaped member tool, the arrangement of the pivot connection and the lost motion connection is such that a major part of the closing force applied to the jaw members by the operating cable is lost, and the closing force applied to the jaws at the end of the cutting stroke, just as the jaws come together to begin cutting the food particle or the tumor, is at a minimum, even though it is at this point that the cutting force should be as large as possible. More specifically, in some of these prior art patents it is believed that because the pivot connection is located between the lost motion camming connection and the extending end of the jaw members, and, as a result, the fulcrum is located too close to the ends of the jaw members to effectively transmit and conserve the force manually applied to the operating cable by the user of the tool, only a minimum closing force is applied to the jaws when they come together at the point where the food particle or tumor is being cut by the jaws.

By contrast, the present invention provides a tool which maximizes the conservation of force at the point where cutting occurs, and provides significantly improved results as compared to known tools of the type described above.

SUMMARY OF THE INVENTION

In accordance with the present invention, a tool is provided for cutting and/or grasping pieces of food particles or human tissue which comprised a pair of jaw members, each having a generally similar extending length, with one of the jaw members being relatively fixed and with one of the jaw members being relatively movable with respect to the other. A first pivot connection between the pair of jaw members is located at one end thereof, and comprises a first slot formed in one of the jaw members that extends along an axis generally parallel to the extending length of such jaw member, and a first pivot pin fixed to the other of the jaw members and disposed in the first slot. A second camming connection between the pair of jaw members is located between the first pivot connection and the extending ends of the jaw members, and includes a second slot formed in one of the jaw members that extends along an axis disposed at an acute angle to the extending length of the one jaw member, and a second pin fixed to the other of the jaw members and disposed in the second slot. An operating member is attached to the relatively movable jaw member at its end opposite its extending end and arranged to exert on the movable jaw member a pulling and pushing force directed generally parallel to the extending length of the relatively fixed jaw member, such pulling force causing the movable jaw member to have a first pivotable component of movement about the first pivot connection relative to the fixed jaw member, and to have a second lateral component of movement about the second camming connection to cause the movable jaw member to move laterally relative to the fixed jaw member in a direction generally parallel to the extending length thereof and in a direction generally toward the first pivot connection, whereby the first pivot connection and the second camming connection cooperate to cause a large portion of such pulling force to be applied to the movable jaw member during its movement toward the fixed jaw member.

In the preferred embodiment of the present invention, the movable jaw member has a pointed hook portion formed at the extending thereof, and the fixed jaw member is formed with an enlarged opening for receiving therein the movable jaw member when the pulling force is applied to the movable jaw member. The fixed jaw member is formed with a cutting edge portion adjacent its extending end, and, when the aforesaid pulling force is applied to the movable jaw member, the hook portion of the movable jaw member is caused to move inwardly relative to such cutting edge portion and in close proximity thereto by the aforesaid second lateral component of movement.

DESCRIPTION OF THE PREFERRED EMBODIMENT

Figure 1:
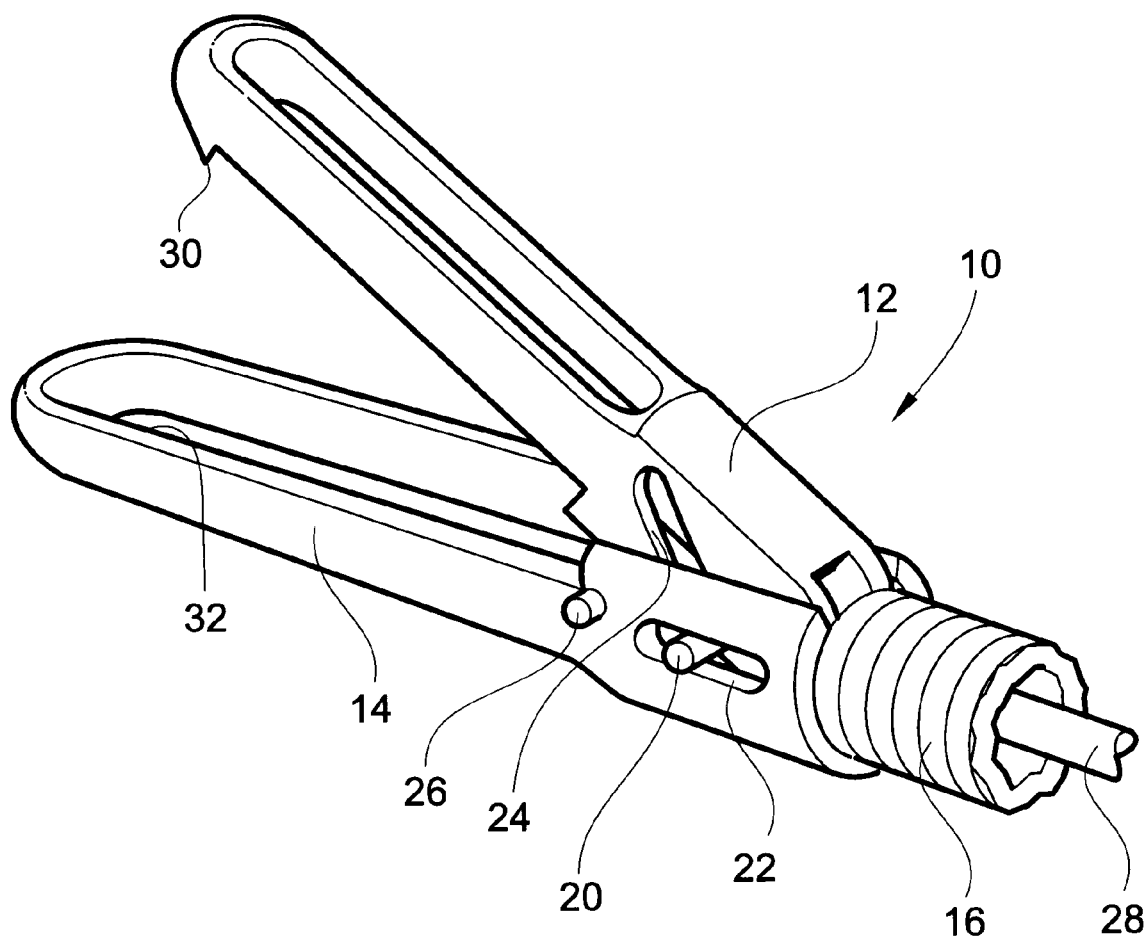
FIG. 1 is a perspective view illustrating the preferred embodiment of the tool of the present invention.
Figure 2:
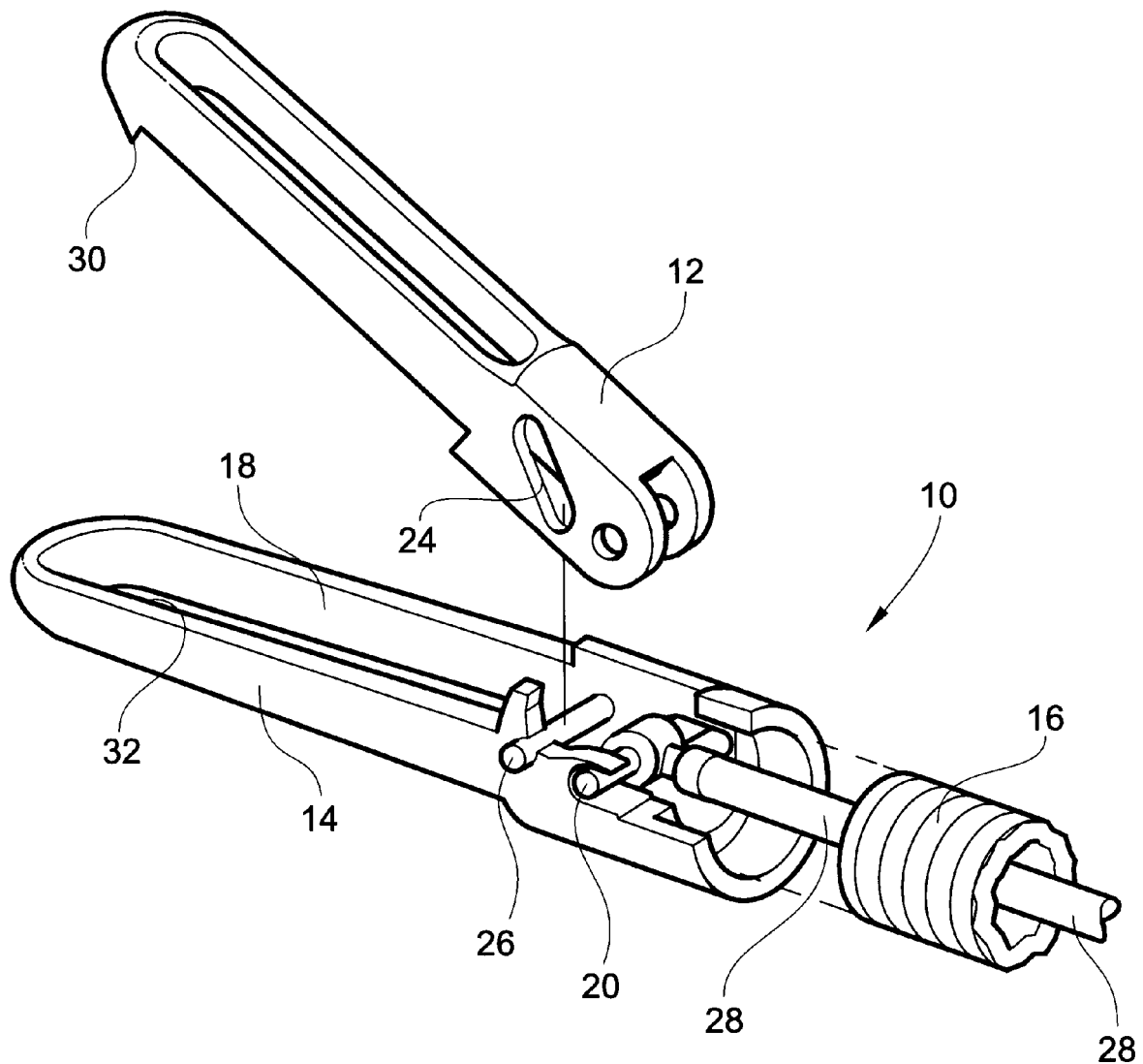
FIG. 2 is a perspective view similar to FIG. 1, but partially broken away and exploded to illustrate the internal parts of the tool.

Looking now in greater detail at the accompanying drawings, FIGS. 1 and 2 illustrate the preferred embodiment of the tool 10 of the present invention, which includes a first upper jaw member 12 and a lower jaw member 14, each of which extends laterally from a sheath member 16. For clarity of understanding, the upper jaw member 12 will be referred to as the movable jaw member, and the lower jaw member 14 will be referred to as the fixed jaw member, but it will be understood that either or both of the jaw members 12,14 could actually move, and it is the relative movement between the two jaw members 12,14 which is significant rather than which jaw member 12,14 is actually moving.

The fixed jaw member 14 is formed with an enlarged opening 18, and the movable jaw member 12 is carried within the enlarged opening 18, and one end of the movable jaw member 12 is pivotally connected to the fixed jaw member 14 by a first pivot connection which includes a pivot pin 20 that extends through the end of the movable jaw member 12 in perpendicular relation to the extending length thereof, and each end of the pin 20 extends outwardly from the movable jaw member 12 so as to be disposed in slots 22 formed in the fixed jaw member 14. Only one of the slots 22 is illustrated in FIG. 1, but it will be readily understood that an identical slot is formed in the opposite side of the fixed jaw member 14 in the same manner as that illustrated in FIGS. 1 and 2. The slots 22 extend along an axis that is generally parallel to the extending length of the fixed jaw member 14, and the extending ends of the pin 20 slides within the slots 22 in a manner to be described in greater detail below. A second slot motion connection is provided between the jaw members 12,14 in the form of a second pair of slots 24 formed in the movable jaw member 12 and, again, only one of which is visible in FIG. 1 but it will be understood that an identical slot is also formed on the opposite side of the movable jaw member 12. A second pin 26 is mounted in the fixed jaw member 14 and extends across the enlarged opening 18, and through both of the slots 24 in the movable jaw member 12. The slot 24 extends along an axis disposed at an acute angle to the extending length of the movable jaw member 12. It will also be noted that the second slot motion connection, consisting of the pin 26 and the slots 24, is located intermediate the extending ends of the jaw members 12,14 and the second pivot connection comprised by the slots 22 and the pin 20, and the significance of this arrangement will be explained in greater detail below.

The end of the movable jaw member 12, which contains the pin 20, is connected in any convenient manner to an operating cable 28, and this operating cable 28 extends outwardly through the sheath 16 to a conventional operating member (not shown) which moves the operating cable 28 axially within the sheath 16 to exert a pushing force on the end of the movable jaw member 12 when the operating cable 32 is moved in a direction towards the tool 10, and a pulling force on the movable jaw member 12 when the operating cable 28 is moved in a direction away from the tool 10.

The extending end of the movable jaw member is formed with a pointed hook portion 30, and the corresponding extending end portion of the fixed jaw member 14 is provided with a cutting edge 32 disposed along the upper periphery of the fixed jaw member 14.

In general, it will be apparent from the description above that when the operating cable 28 moves outwardly away from the tool 10, the movable jaw member 12 will pivot downwardly relative to the fixed jaw member 14, and the details of that movement can best be understood by reference to FIGS. 3A–3D and FIG. 4.

Figure 3A:
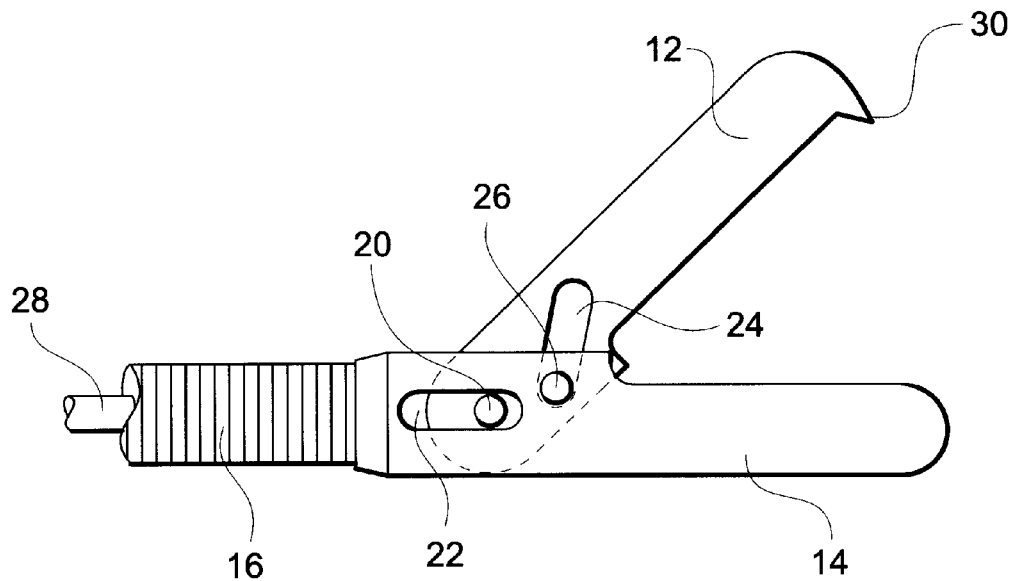
FIGS. 3A–3D are diagrammatic views showing the relative positions of the jaw members of the tool during closing movement of the relatively movable jaw member.
Figure 3B:
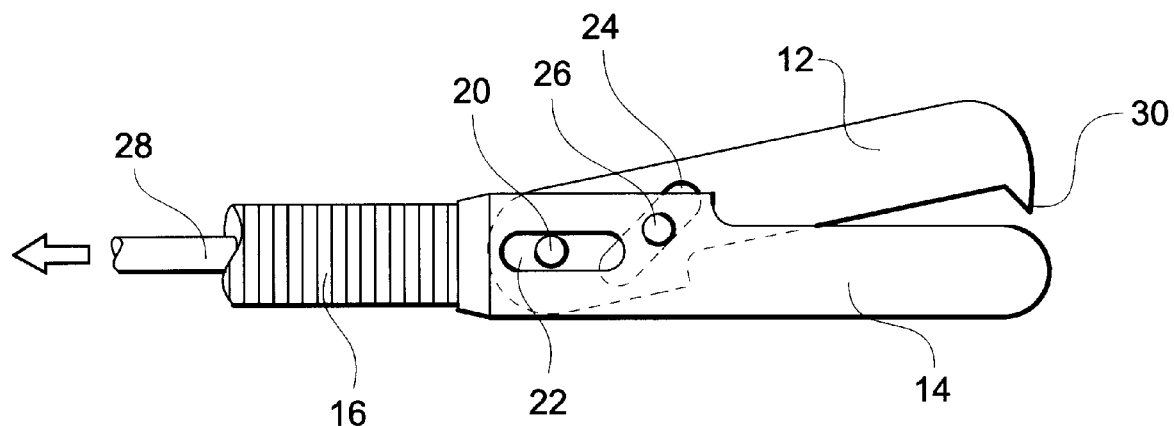
Figure 3C:
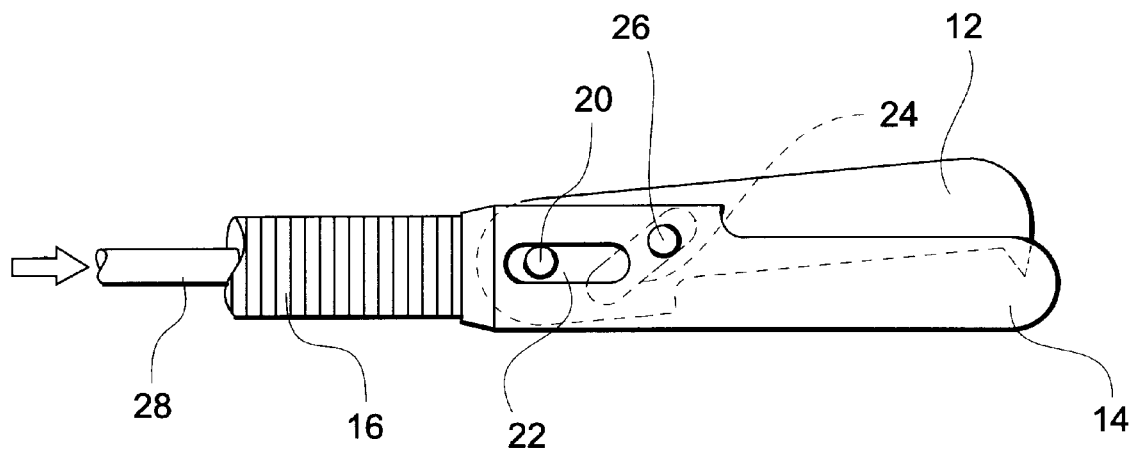

More specifically, FIG. 3A shows the jaw members 12,14 in their fully open position, which occurs when the cable 28 is moved in a direction toward the tool 10, or to the right in FIG. 3A. To close the jaw members 12,14, the operating cable 28 is moved in the opposite direction as indicated by the direction arrows in FIGS. 3B and 3C, which causes the pivot pin 20 to move laterally within the slots 22 and, simultaneously, causes the slots 24 in the movable jaw member 12 to be moved over the lost motion pivot pin 26 as illustrated in FIGS. 3A–3D. By virtue of this unique arrangement of the two pivot pins 20,26, both operating in cooperating slots 22,24, respectively, and the relative location of the lost motion pivot pin 26 being positioned between the pivot pin 20 and the extending end of the jaw members 12,14, it has been found that two significant benefits are obtained in connection with the movement of the jaw members 12,14. First, as illustrated by the relative position of the movable jaw member in FIGS. 3B, 3B, and 3C, the movable jaw member 12 is moved inwardly (to the left) relatively to the stationary jaw member 14 and its cutting edge 32, and this relative lateral movement of the jaw members 12,14 provides an enhanced cutting action between the jaw members 12,14 at the cutting edge 32, as compared with the conventional pivot movement of prior art jaw members where there is only pivotal movement toward one another, with no lateral movement component.

Figure 3D:
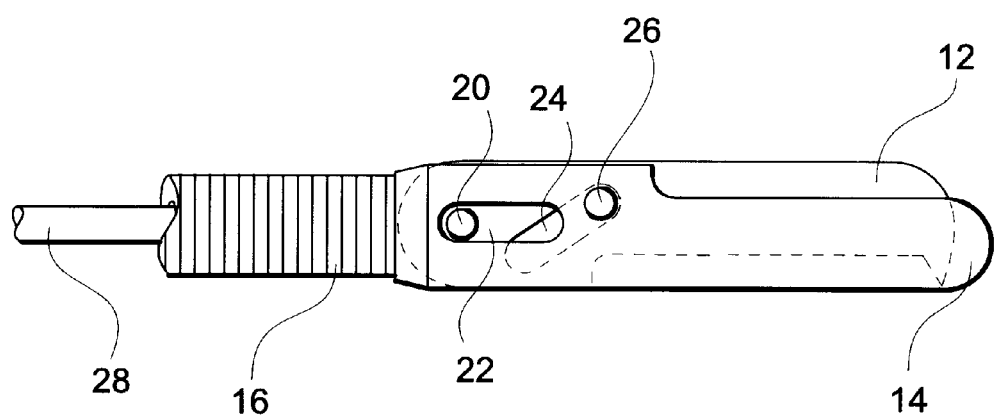

Additionally, and importantly, the aforesaid relationship between the pins 20,26 and the cooperating slots 22,24 result in an increased closing force being applied to the jaw members 12,14 as they approach the fully closed position illustrated in FIG. 3D. As indicated above, conventional prior art jaw members have a maximum force component at the point where the pivoted jaws are in their most open position and begin movement towards their closed position and, as a result, the closing force is at a minimum at the point where the two jaws come together, which is precisely the point at which maximum force is desired because it is at this point that the jaws are grasping or cutting food particles and/or in the tissue.

Figure 4:
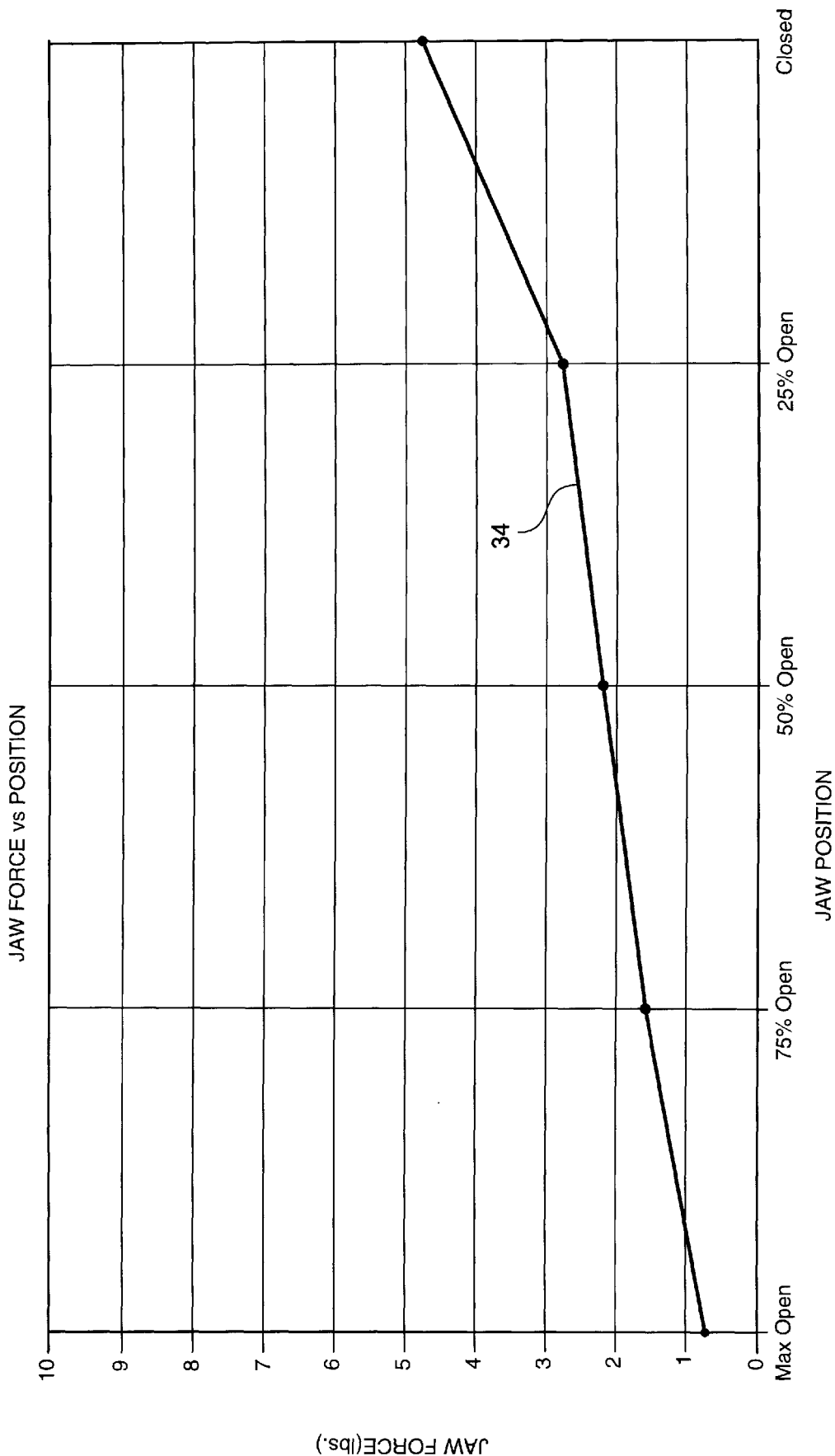
FIG. 4 is a chart showing the force being applied to the jaws by the operating cable of the tool at the positions of the jaw members illustrated in FIGS. 3A–3D.

It has been found that the unique arrangement of the present invention actually results in a maximum closing force being applied to the jaws at the point where they come together. These forces are plotted in the graph illustrated in FIG. 4, where the X-axis represents the relative position of the jaw members 12,14, and the Y-axis represents the closing force applied to the jaws in pounds (lbs). This particular graph is based on a ten-pound input of force to the operating cable 28, which is an approximate average input force that would be applied by a typical nurse. It will be understood, of course, that some of the ten-pound force applied to the operating cable 28 will be lost through friction and other operating inefficiencies and, therefore, the line 34 which is plotted in FIG. 4, represents a maximum conservation of the input force. The line 34 plotted in FIG. 4 was arrived at empirically using a vector analysis derived from the relationship of the pins 20,26 and the slots 22,24, respectively, and it is significant to note that the closing force applied to the jaws gradually increases as it moves from its maximum open position to its 50% open position, to its 25% open position, and then to its final closed position.

Accordingly, as the jaw members 12,14 come together at the point where a food product and/or human tissue are to be grasped and/or cut by the jaw members, the maximum cutting force is applied to the jaws 12,14 at that point.

This significant advantage, combined with the lateral movement of the movable jaw member 12 relative to the fixed jaw member 14 as described above provides a significantly improved operation of the jaw members 12–14 for their intended purpose.

It will therefore be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A tool for cutting and/or grasping pieces of food particles or human tissue, said tool comprising:
   (a) a pair of jaw members, each having one end an extending end and a generally similar extending length, therebetween with one of said jaw members being relatively fixed and with one of said jaw members being relatively movable with respect to the other;
   (b) a first pivot connection between said pair of jaw members located at one end thereof, said first connection comprising a first slot formed in one of said jaw members that extends along an axis generally parallel to the extending length of said one jaw member, and a first pivot pin fixed to the other of said jaw members and disposed in said first slot:
   (c) a second camming connection between said pair of jaw members located between said first pivot connection and the extending ends of said jaw members, said second camming connection including a second slot formed in one of said jaw members that extends along an axis disposed at an acute angle to said extending length of said one jaw member, and a second pin fixed to the other of said jaw members and disposed in said second slot; and
   (d) an operating member attached to said relatively movable jaw member at its end opposite its said extending end and arranged to exert on said movable jaw member a pulling and pushing force directed generally parallel to the extending length of said relatively fixed jaw member, said pulling force causing said movable jaw member to have a first pivotable component of movement about said first pivot connection relative to said fixed jaw member, and to have a second lateral component of movement about said second camming connection to cause said movable jaw member to move laterally relative to said fixed jaw member in a direction generally parallel to the extending length thereof and in a direction generally toward said first pivot connection, whereby said first pivot connection and said second camming connection cooperate to cause said pulling force to be applied to said movable jaw member in an increasing amount during its movement toward said fixed jaw member.

2. A tool as defined in claim 1, wherein said movable jaw member has a pointed hook portion formed at the extending thereof.

3. A tool as defined in claim 2, wherein said fixed jaw member is formed with an enlarged opening for receiving therein said movable jaw member when said pulling force is applied to said movable jaw member, wherein said fixed jaw member is formed with a cutting edge portion adjacent its extending end, and wherein said hook portion of said movable jaw member is caused to move inwardly relative to said cutting edge portion and in close proximity thereto by said second lateral component of movement when said pulling force is applied to said movable jaw member.

4. A tool as defined in claim 1, wherein said first slot is formed in said fixed jaw member, and wherein said second slot is formed in said movable jaw member.

5. A tool for cutting and/or grasping pieces of food particles or human tissue, said tool comprising:
   (a) a first relatively fixed jaw member having an inner end portion an extending end and an extending length therebetween, said fixed jaw member having an enlarged opening formed therein terminating at its extending end with a cutting edge portion;
   (b) a second relatively movable jaw member having an inner end portion and an extending length therefrom, said movable jaw member having a pointed hook portion formed at the extending end thereof;
   (c) a first pivot connection between said pair of jaw members located adjacent said inner ends thereof comprising a first slot formed in said fixed jaw member that extends along an axis generally parallel to the extending length of said fixed jaw member, and a first pivot pin fixed to said movable jaw member and disposed in said first slot:
   (d) a second camming connection between said first and second jaw members located between said first pivot connection and the extending ends of said first and second jaw members, said second camming connection including a second slot formed in said movable jaw member that extends along an axis disposed at an acute angle to said extending length of said movable jaw member, and a second pin fixed to said fixed jaw member and disposed in said second slot; and
   (e) an operating member attached to said inner end of said movable jaw member and arranged to exert on said movable jaw member a pulling and pushing force directed generally parallel to the extending length of said fixed jaw member, said pulling force causing said movable jaw member to have a first pivotable component of movement about said first pivot connection relative to said fixed jaw member, and to have a second lateral component of movement about said second camming connection to cause said movable jaw member to move laterally relative to said fixed jaw member in a direction generally parallel to the extending length thereof and in a direction generally toward said first pivot connection, said first pivot connection and said second camming connection cooperating to cause an increasing portion of said pulling force to be applied to said movable jaw member during its movement toward said fixed jaw member, and to cause said hook portion of said movable jaw member to be moved inwardly relative to said cutting edge portion of said fixed jaw member and in close proximity thereto by said second lateral component of movement when said pulling force is applied to said movable jaw member.

* * * * *